US009072442B2

(12) United States Patent
Krupnik (10) Patent No.: US 9,072,442 B2
(45) Date of Patent: Jul. 7, 2015

(54) SYSTEM AND METHOD FOR DISPLAYING AN IMAGE STREAM (75) Inventor: Hagai Krupnik, Nofit (IL)

(73) Assignee: GIVEN IMAGING LTD., Yoqneam (IL)

( * ) Notice: Subject to any disclaimer, the term of this patent is extended or adjusted under 35 U.S.C. 154(b) by 1726 days.

(21) Appl. No.: 11/358,401

(22) Filed: Feb. 22, 2006

(65) Prior Publication Data

US 2006/0164511 A1 Jul. 27, 2006

Related U.S. Application Data

(63) Continuation-in-part of application No. PCT/IL2004/001181, filed on Dec. 29, 2004.

(60) Provisional application No. 60/533,263, filed on Dec. 31, 2003.

(51) Int. Cl.
*A61B 1/04* (2006.01)
*A61B 5/07* (2006.01)
*G06F 19/00* (2011.01)
*H04N 7/18* (2006.01)
(Continued)

(52) U.S. Cl.
CPC ............ *A61B 1/041* (2013.01); *A61B 1/00009* (2013.01); *A61B 1/0005* (2013.01); *A61B 1/04* (2013.01); *A61B 5/0008* (2013.01); *A61B 5/036* (2013.01); *A61B 5/073* (2013.01); *A61B 5/145* (2013.01); *A61B 5/14539* (2013.01); *A61B 5/7435* (2013.01); *A61B 5/7445* (2013.01); *A61B 5/7475* (2013.01); *A61B 2560/045* (2013.01); *G06F 19/321* (2013.01); *G06F 19/3406* (2013.01); *H04N 7/181* (2013.01)

(58) Field of Classification Search
CPC .............................. A61B 1/041; A61B 1/0005
USPC .............. 600/109, 407, 101, 160; 348/65, 78, 348/207.99, 207.1, 208.14, 211.2; 455/66, 455/95, 100; 382/128
See application file for complete search history.

(56) References Cited

U.S. PATENT DOCUMENTS 4,243,652 A 1/1981 Francis
4,278,077 A 7/1981 Mizumoto
(Continued)

FOREIGN PATENT DOCUMENTS

DE 344 0177 5/1986
JP 5745833 3/1982
(Continued)

OTHER PUBLICATIONS

Lehmann, Tomas, Content-Based Image Retrieval in Medical Applications: A Novel Multi-Step Approach, SPIE 2000, pp. 1-3.*
(Continued)

*Primary Examiner* — Rochelle Turchen
(74) *Attorney, Agent, or Firm* — Pearl Cohen Zedek Latzer Baratz LLP (57) ABSTRACT

A system and method may display an image stream, where an original image stream may be divided into two or more subset images streams, each subset image stream being displayed simultaneously or substantially simultaneously. The spatial position of the images displayed substantially simultaneously in each time slot may be variably adjusted based on a predetermined criterion. The images may be collected from an ingestible capsule traversing the GI tract.

22 Claims, 8 Drawing Sheets

(51) Int. Cl.
*A61B 1/00* (2006.01)
*A61B 5/00* (2006.01)
*A61B 5/03* (2006.01)
*A61B 5/145* (2006.01)

(56) References Cited

U.S. PATENT DOCUMENTS

| | | | |
|---|---|---|---|
| 4,698,664 | A | 10/1987 | Nichols et al. |
| 4,907,095 | A | 3/1990 | Komura et al. |
| 5,381,784 | A | 1/1995 | Adair |
| 5,566,169 | A | 10/1996 | Rangan et al. |
| 5,603,687 | A | 2/1997 | Hori et al. |
| 5,604,531 | A * | 2/1997 | Iddan et al. ............... 348/76 |
| 5,605,153 | A * | 2/1997 | Fujioka et al. ............ 600/425 |
| 5,642,157 | A | 6/1997 | Shibanuma |
| 5,697,885 | A | 12/1997 | Konomura et al. |
| 5,726,670 | A | 3/1998 | Tabata et al. |
| 5,880,777 | A | 3/1999 | Savoye et al. |
| 5,993,378 | A | 11/1999 | Lemelson |
| 6,173,317 | B1 | 1/2001 | Chaddha et al. |
| 6,208,354 | B1 | 3/2001 | Porter |
| 6,240,312 | B1 | 5/2001 | Alfano et al. |
| 6,289,165 | B1 | 9/2001 | Abecassis |
| 6,504,990 | B1 | 1/2003 | Abecassis |
| 6,563,959 | B1 * | 5/2003 | Troyanker ............... 382/282 |
| 6,709,387 | B1 * | 3/2004 | Glukhovsky et al. ...... 600/109 |
| 6,741,977 | B1 | 5/2004 | Nagaya et al. |
| 6,764,440 | B2 | 7/2004 | Iddan et al. |
| 6,902,581 | B2 | 6/2005 | Walkenhorst et al. |
| 6,904,308 | B2 | 6/2005 | Frisch et al. |
| 6,944,316 | B2 * | 9/2005 | Glukhovsky et al. ...... 382/107 |
| 6,976,229 | B1 | 12/2005 | Balabanovic et al. |
| 7,027,633 | B2 | 4/2006 | Foran et al. |
| 7,119,814 | B2 * | 10/2006 | Meron et al. .............. 345/619 |
| 7,200,253 | B2 * | 4/2007 | Glukhovsky et al. ...... 382/128 |
| 7,272,657 | B2 | 9/2007 | Allen et al. |
| 7,324,673 | B1 | 1/2008 | Yamanaka et al. |
| 7,392,233 | B2 * | 6/2008 | Tanaka ................... 707/1 |
| 2001/0015753 | A1 | 8/2001 | Myers |
| 2001/0035902 | A1 | 11/2001 | Iddan et al. |
| 2002/0021828 | A1 * | 2/2002 | Papier et al. ............. 382/128 |
| 2002/0103417 | A1 | 8/2002 | Gazdzinski |
| 2002/0109774 | A1 | 8/2002 | Meron et al. |
| 2002/0140861 | A1 | 10/2002 | Janevski et al. |
| 2002/0177779 | A1 | 11/2002 | Adler et al. |
| 2003/0086596 | A1 | 5/2003 | Hipp et al. |
| 2003/0151661 | A1 * | 8/2003 | Davidson et al. .......... 348/65 |
| 2003/0174208 | A1 | 9/2003 | Glukhovsky et al. |
| 2004/0027500 | A1 | 2/2004 | Davidson et al. |
| 2004/0249291 | A1 | 12/2004 | Honda et al. |
| 2005/0038321 | A1 | 2/2005 | Fujita et al. |
| 2005/0074151 | A1 * | 4/2005 | Chen et al. .............. 382/128 |
| 2005/0075537 | A1 | 4/2005 | Chen et al. |
| 2005/0110948 | A1 | 5/2005 | Bille |
| 2006/0036131 | A1 * | 2/2006 | Glukhovsky et al. ...... 600/160 |
| 2006/0106318 | A1 | 5/2006 | Davidson |
| 2006/0164511 | A1 | 7/2006 | Krupnik |
| 2006/0187300 | A1 | 8/2006 | Davidson et al. |
| 2009/0135250 | A1 | 5/2009 | Davidson et al. |

FOREIGN PATENT DOCUMENTS

| | | |
|---|---|---|
| JP | 61-143876 | 7/1986 |
| JP | 63-214231 | 9/1988 |
| JP | 02-286124 | 11/1990 |
| JP | 4109927 | 4/1992 |
| JP | 4-144533 | 5/1992 |
| JP | 1992-144533 | 5/1992 |
| JP | 2000-047651 | 2/2000 |
| JP | 2001-167248 | 6/2001 |
| JP | 2002-503046 | 1/2002 |
| JP | 2002-159472 | 6/2002 |
| JP | 2003-038424 | 2/2003 |
| JP | 2003-135387 | 5/2003 |
| JP | 2005-157227 | 6/2005 |
| WO | WO 99/40587 | 8/1999 |
| WO | WO 00/22975 | 4/2000 |
| WO | WO 01/50180 | 7/2001 |
| WO | WO 01/50941 | 7/2001 |
| WO | WO 01/65995 | 9/2001 |
| WO | WO 02/054932 | 7/2002 |
| WO | WO 2005/062715 | 7/2005 |

OTHER PUBLICATIONS

Rubner, Yossi, Empirical Evaluation of Dissimilarity Measures for Color and Texture, Computer Vision and Image Understanding 84, 2001, pp. 25-43.*
International Search Report for PCT Application No. PCT/IL04/01181 mailed Feb. 24, 2006.
U.S. Appl. No. 60/355,796, filed Feb. 12, 2002, Davidson et al.
www.zdnet.co.uk/pcmag/trends/2001/04/06.html, "perfect Motion on the Net"—Cliff Joseph, printed Dec. 25, 2001.
www.dynapel.com Motion Perfect products literature, printed Jul. 22, 2003.
Office Action of U.S. Appl. No. 10/610,915 dated Feb. 7, 2008.
Office Action of U.S. Appl. No. 10/610,915 dated Oct. 27, 2006.
"Synchronized nQUAD Technology", www.cartesiantech.com.
Yang et al., "Two Image Photometric Stereo Method", Department of Information Engineering, Nagoya University, SPIE, vol. 1826, intelligent Robots and Computer Vision XI, 1992, pp. 452-463.
Office Action for U.S. Appl. No. 10/986,918 dated Sep. 22, 2005.
Office Action for U.S. Appl. No. 10/986,918 dated Apr. 6, 2006.
Office Action of U.S. Appl. No. 10/364,508 mailed on Jan. 23, 2007.
Office Action of U.S. Appl. No. 10/364,508 mailed on Jun. 5, 2007.
Office Action of U.S. Appl. No. 10/364,508 dated Jun. 7, 2006.
Final Office Action of U.S. Appl. No. 10/610,915 dated May 17, 2007.
Office Action of U.S. Appl. No. 10/364,508 dated Jan. 23, 2008.
Office Action of U.S. Appl. No. 10/584,997 Dated Mar. 30, 2009.
EU Search Report dated Nov. 9, 2009, issued in Patent Application No. EP 04 806712.
Office Action in U.S. Appl. No. 10/584,997 dated Sep. 14, 2009.
Office Action of U.S. Appl. No. 10/584,997 dated Jan. 14, 2010.
Japanese Notice of Allowance, issued Apr. 13, 2010, for Japanese Application No. 2006-160094.
Final Office Action, issued Jul. 9, 2010, for U.S. Appl. No. 10/584,997.
Office Action, issued Jun. 25, 2010, for U.S. Appl. No. 11/321,456.
Office Action, issued Dec. 3, 2010, for U.S. Appl. No. 11/321,456.
Japanese Office Action, mailed Jun. 28, 2010, for Japanese Application No. 2006-546478.
Office Action, issued Feb. 17, 2011, for U.S. Appl. No. 10/584,997.
Office Action, issued Feb. 4, 2011, for U.S. Appl. No. 12/323,620.
Final Office Action issued for U.S. Appl. No. 10/584,997 and dated Aug. 31, 2011.
Japanese Office Action issued for JP 2006-546478, dated Dec. 13, 2011.
Notice of Allowance issued for U.S. Appl. No. 10/584,997, dated Dec. 14, 2011.

* cited by examiner

SYSTEM AND METHOD FOR DISPLAYING AN IMAGE STREAM

CROSS-REFERENCE TO RELATED APPLICATIONS

This application is a Continuation In Part of International Application PCT/IL2004/001181, entitled "System and method for displaying an image stream" filed Dec. 29, 2004, which in turn claims priority from U.S. application 60/533,263 filed on Dec. 31, 2003, both of which are incorporated by reference in their entirety.

FIELD OF THE INVENTION

The present invention relates to a method and system for displaying and/or reviewing image streams.

BACKGROUND OF THE INVENTION

An image stream may be assembled from a series of still images and displayed to a user. The images may be created or collected from various sources. For example, a known in-vivo imaging system which includes a swallowable capsule, may, for example, capture images of a lumen such as the gastrointestinal (GI) tract and may transmit them to an external recording device. Large numbers of images may be collected for viewing and, for example, combined in sequence. An image stream of, for example, 40 minutes in length, containing for example about 4,800 frames, may be available to, for example a health professional for review. Other numbers of frames or lengths may be used. In one embodiment, a health professional may, for example, use the images to diagnose pathological conditions of the GI tract, and, in addition, the system may provide information about the location of these pathologies. Pathology, if present may typically be found in only a few locations along the long traverse of the GI tract, and therefore in a small percentage of the recorded images.

In general, if possible, a user may try to set the streaming rate to the highest rate where the user can quickly review the image stream without missing important information that may be present in any of the images included in the stream. The rate at which a user can effectively review an image stream may be limited by a physiological averaging above which certain details in individual images displayed in the stream may be physiologically filtered out.

SUMMARY OF THE INVENTION

The system and method according to some embodiments of the present invention may allow an image stream to be viewed while emphasizing images that may be of interest (e.g., images of pathologies). Thus, a user may quickly locate selected images of interest out of a lengthy image stream and an efficient and short view time may be provided. Other uses or benefits of an image display method according to some embodiments of the invention may exist.

In one embodiment, a system and method are provided for displaying an image stream, such that multiple images from the image stream are displayed substantially simultaneously in a time slot. Substantially simultaneously may include simultaneously. As such a single-frame stream display may be converted to a multi-frame stream display that may be shorter in viewing time. In a further embodiment of the invention, the spatial position of the images displayed substantially simultaneously in each time slot may be variably adjusted based on a predetermined criterion. For example, the spatial order or position of the images displayed substantially simultaneously in each time slot may correspond to a degree of variation of each image compared to a selected or generated reference image. In a further example, images displaying pathological looking tissue may be positioned away from images displaying healthy looking tissue. In one embodiment of the invention, images from a group of images displayed substantially simultaneously, containing a high degree of variation as compared to the other images in the group may be displayed in a spatial position where a viewer may typically draw his/her eyes first. In certain embodiments, the images may be collected from an autonomous capsule traversing the GI tract.

In yet another embodiment of the present invention, image frames in an image stream may be sorted based on the similarity between the images included in the image stream such that image frames that show a high degree of similarity may be positioned in one section of the image stream and images that show a high degree of variation may be placed in another section of the image stream. In one example, the sorted image stream may be displayed as a single image stream. In another example, the sorted image stream may be displayed as a plurality of image streams displayed substantially simultaneously.

BRIEF DESCRIPTION OF THE DRAWINGS

The present invention will be understood and appreciated more fully from the following detailed description taken in conjunction with the drawings in which.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

Figure 1A:
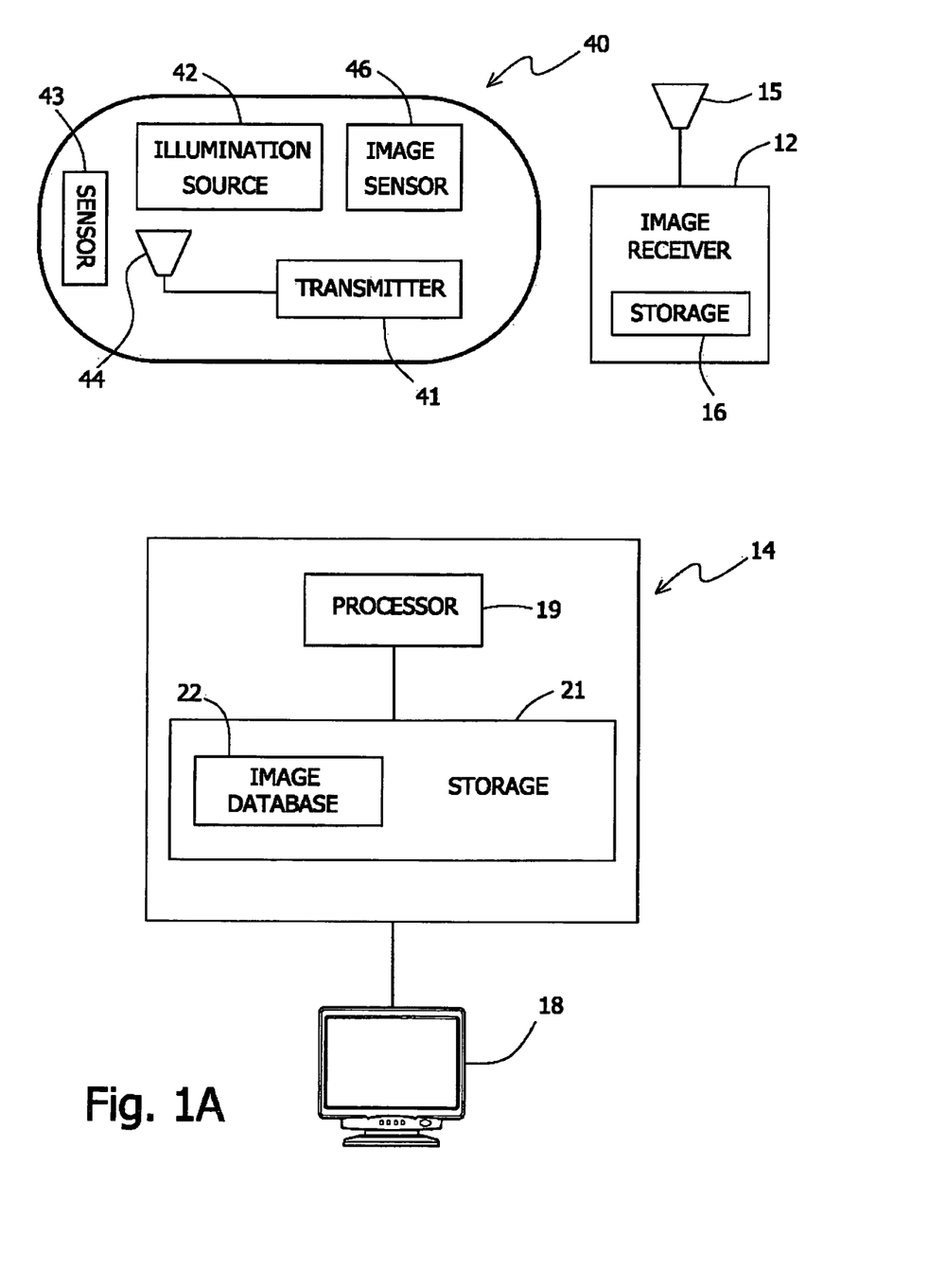
FIG. 1A shows a schematic diagram of an in-vivo imaging system according to one embodiment of the present invention.

Reference is made to FIG. 1A, which shows a schematic diagram of an in-vivo imaging system according to one embodiment of the present invention. In an exemplary embodiment, the system may include an imaging device 40, such as for example a capsule having an image sensor 46, for capturing images, an illumination source 42, for illuminating the body lumen, a transmitter 41, and an antenna 44, for transmitting images and possibly other information to, for example, a receiving device. Typically, the imaging device may correspond to embodiments described in U.S. Pat. No. 5,604,531 to Iddan et al., and to embodiments described in published application WO01/65995 to Glukhovsky et al., both of which are incorporated herein by reference in their entirety, but in alternate embodiments there may be other types of imaging devices. In one embodiment, an imaging device may include more than one image sensor. The image sensors may, for example be arranged at either end of device 40, or at the same end of the device, in slightly different positions or different angles. A device which includes a plurality of image sensors, is described for example, in International Publication Number WO 02/054932 entitled "System and Method for Wide Field Imaging of Body Lumens" which is assigned to the common assignee of the present invention and which is hereby incorporated by reference. Each image sensor may capture in vivo images and transmit the in vivo images via the transmitter 41 or via separate transmitters. The separate in vivo image streams captured may be combined into a single in vivo image stream based on image comparison between the two streams or based on other criteria.

In another embodiment of the invention, device 40 may include, for example, sensors 43 that may be a sensor other than image sensors such as for example, temperature sensor, pressure sensor, blood sensor, pH sensor, ultrasound sensor, oxygen sensor, other sensor, and/or more than one sensor. Data sampled from sensor 43 may, for example, be transmitted via transmitter 41 or via separate transmitters.

Typically, located outside the patient's body in one or more locations may be an image receiver 12, a data processor 14, and an image monitor 18. Image receiver 12 may typically include an antenna or antenna array 15 and an image receiver storage unit 16. Data processor 14 may include, for example, a processor 19 and a storage unit 21. In one embodiment of the present invention, storage unit 21 may include, for example, an image database 22. Image monitor 18 may display, inter alia, images transmitted by, for example, device 40. Typically, data processor 14 and monitor 18 may be part of a personal computer or workstation, which includes standard components such as processor 19, a memory, a disk drive, and input-output devices, although alternate configurations are possible. Data processor 14 may typically, as part of its functionality, acts as a controller controlling the display of the images. Image monitor 18 may typically be a conventional video display, but may, in addition, be any other device capable of providing images or other data and may be of any size monitor including small palm type monitors or large projection size monitors. The image monitor 18 presents the image data, typically in the form of still and streaming image frames, and in addition may present other information. In an exemplary embodiment, the various categories of information are displayed in windows. Other displaying formats may be used. Multple monitors may be used to display image and other data. The images captured by the imaging system may be of any suitable shape including for example circular, square, rectangular, or hexagonal, oval etc.

According to one example data processor 14 and/or image receiver 12 may include a user input device for entering commands and/or entering information, e.g. a key board, mouse, joystick, etc. In one example processor 14 may sort a plurality of image frames and may control display of the sorted plurality of image frames in the sorted order as an image stream. Display and/or display 18 may display the sorted image stream. In another example, the sorting may be performed by a processor other than processor 14, for example, a processor included in receiver 12.

In operation, image sensor 46 may capture images and may send data, for example, image data to transmitter 41, which may transmit data to receiver 12 using, for example, electromagnetic radio waves. Other types of data other than image data may be transmitted. Receiver 12 may transfer the data to receiver storage unit 16. Image data stored in storage unit 16 may be transferred to the data processor 14 and/or the data processor storage unit 21. For example, the receiver 12 or receiver storage unit 16 may be taken off the patient's body and may be connected to the personal computer or workstation that may include the data processor 14 via a standard data link, e.g., a serial, parallel, USB, or wireless interface of known construction. The data, for example, image data may then be transferred from the receiver storage unit 16 to a database 22 that may be included in data processor storage unit 21. Typically, the image stream is stored as a series of images in the image database 22, which may be implemented in a variety of known manners. Data processor 14, including dedicated software may analyze the data and provide the analyzed data to the image monitor 18, where a user may view the image data and/or other data. In one embodiment of the invention, more than one image stream may be captured from more than one image sensor. In this embodiment, data processor 14 may be used to combine the separate image streams into one image stream. The combining of the two or more image streams may be for example, based on comparing images from each image stream, based on time of image capture, or based on other criteria or more than one criterion. Other configurations may allow for real time viewing where, for example, device 40 or receiver 12 may transmit data in real time to data processor 14 for real time viewing on monitor 18.

Typically, according to one embodiment, an in-vivo imaging device, such as for example device 40, collects a series of still images as it may traverse the GI tract. In one embodiment of the present invention, device 40 may collect a large volume of data, as it may take several hours to traverse the GI tract, and may record images at a rate of, for example, two images every second, resulting in the recordation of, for example, thousands of images. The image recordation rate (or frame capture rate) and recordation duration may be varied.

Typically, the data captured and transmitted by the device 40 may be digital color image data, although in alternate embodiments other image formats may be used and data other than and/or in addition to image data may be transmitted. In an exemplary embodiment, each frame of image data may include, for example, 256 rows of 256 pixels, each pixel may include, for example, bytes for color and brightness, according to known methods. In other embodiments, image data may include more a less pixels and each pixel may include other information or other number of bytes. Other suitable methods of recording image data may be used. Typically, images may be stored sequentially in, for example, data processor storage unit 21. In other embodiments, image data and/or other data may be stored in receiver storage 16.

Figure 1B:
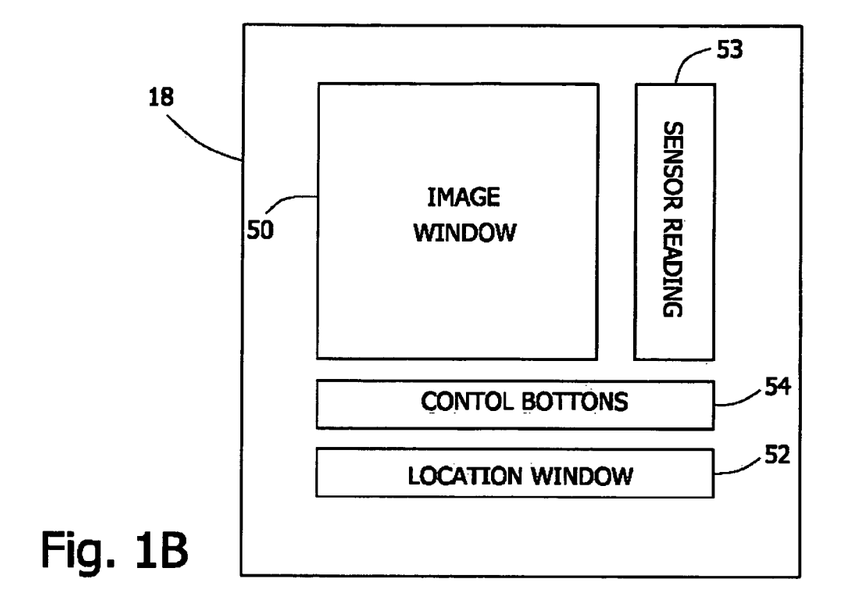
FIG. 1B shows a schematic diagram of a monitor display according to one embodiment of the present invention.

Typically, data processor storage unit 21 may store a series of images captured by device 40, for example, as it moves through a patient's GI tract. The series of images may be combined consecutively to form an image stream. When viewing the image stream, the user may be typically presented with one or more windows on monitor 18; in alternate embodiments multiple windows need not be used and only the image stream may be displayed. Reference is now made to FIG. 1B showing a schematic diagram of display 18. In an embodiment where multiple windows are provided, for example, an image window 50 may display the image stream or still portions of that image stream. A sensor window 53, may display a concurrent stream of data from sensors other than image sensors, for example, ultrasound, pressure, temperature, blood, oxygen, and/or a pH sensor. Other sensors may be used. A location window 52 may display information on the location of the imaging device, for example, device 40, at the time of capturing the image frames being displayed. A control window 54 may include buttons or other controls that may be used to alter the display of the image; for example, stop, play, pause, capture image, step, fast-forward, rewind, or other. Such controls may be activated by, for example, a pointing device such as a mouse or trackball. Typically, the image stream may be frozen to view one frame or one set of frames, speeded up, or reversed; sections may be skipped; or any other method for viewing an image may be applied to the image stream. Other windows may be included.

While the following discussion relates to the case where data from a device 40 is stored for later use, the system and method of the present invention may be used with systems allowing for real time viewing of image data.

Furthermore, while typically the components accepting, processing and displaying the image data are contained within a workstation system or PC, other systems may be used, and other (e.g., distributed) components may perform such image accepting, processing and displaying. For example, a large projection type monitor may be used to view a plurality of images substantially simultaneously.

Figure 6:
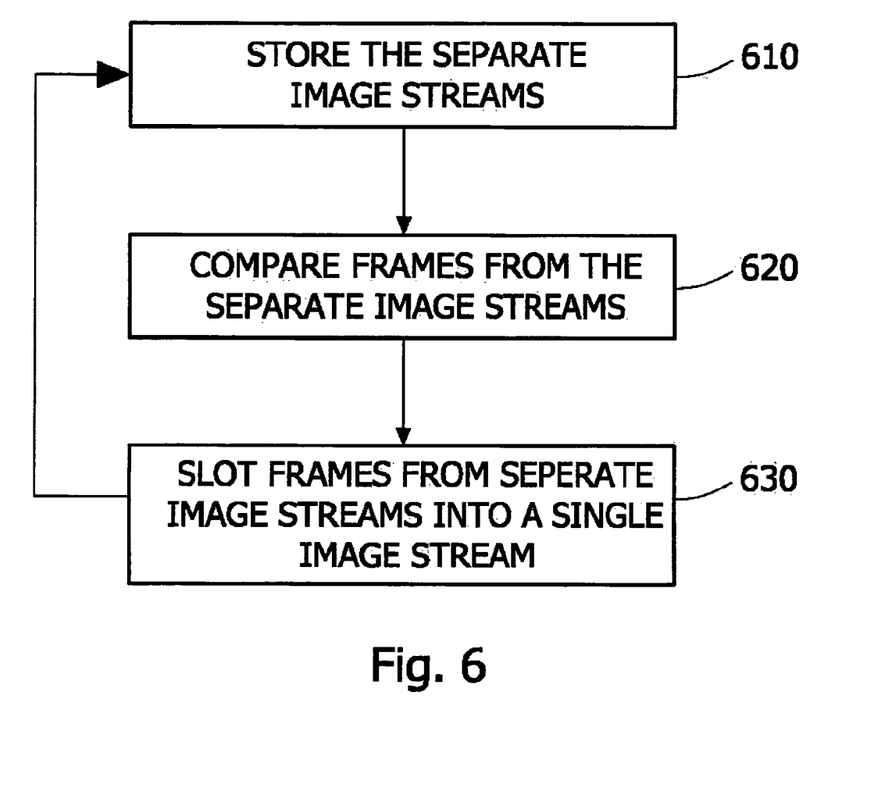
FIG. 6 shows an exemplary flow chart describing a method for combining multiple image streams into a single image stream according to an embodiment of the present invention.

In one embodiment of the present invention, device 40 may have more than one imager. Multiple image streams may result from multiple imagers being in the same device, or possibly by splitting one image stream into multiple images streams. Combining of image streams may be performed by for example a processing device, e.g. processor 19. Reference is now made to FIG. 6, showing an exemplary flow chart describing a method for combining multiple image streams into a single image stream. Each image sensor may capture in vivo images and transmit the in vivo images via the transmitter 41 or via separate transmitters. Alternately, one image stream may be split (e.g., every other image may be placed into one of two image streams, etc.). The separate image streams obtained from the multiple image sensors may be stored (step 610). Comparison may be made between the frames captured from the separate image streams (step 620). In other embodiments of the invention, the separate image streams may not be stored in their entirety before comparison is made. Based on the comparison, frames from each of the separate image streams may be slotted into a single image stream (step 630). Other methods besides or in addition to comparing frames may be used to combine multiple image streams. The separate image streams may be combined such that frames displaying similar scenery are slotted in close proximity to each other. As such, the multiple image streams may be displayed in a variable order and/or manner. Other suitable criteria may be used as well.

In one embodiment, the imaging window (e.g. monitor 18) may display a multi-frame stream where multiple images are displayed substantially simultaneously in each time slot, thereby reducing the viewing time. In one embodiment, processor 19 may determine spatial positioning of each of the frames displayed substantially simultaneously. For example, in one embodiment, the original image stream may be divided into, for example, separate image streams displayed substantially simultaneously in single time slots. Various methods may be used to separate an original image stream into a plurality of image streams to be streamed substantially simultaneously. In one example, images from the original image stream may be divided into, for example, 16 subset image streams such that, for example, during the first time slot, the first 16 images of the original image stream may be displayed substantially simultaneously, and in the second time slot the next 16 images of the original images stream may be displayed substantially simultaneously, etc. Other number of image streams may be used and some frames in the original stream may be skipped. In alternate embodiments, the images may be separated, for example, placed in different files or memory blocks in processor 14. In one embodiment, each resulting image stream may include a separate subset of images from the original image stream; in alternate embodiments, the images from each resulting image stream may overlap. In another embodiment of the invention, images of the original image stream may be divided between the separate images streams in alternate manners that may be suitable. Typically, the spatial positioning and/or order of the frames, for example, the frames obtained from corresponding separate image streams may vary for each time slot.

In one embodiment, images from the original image stream may be simply directed to the proper screen position at viewing time, and the image stream may, for example, not actually be separated in separate image streams. In such embodiments, a different number of images may be displayed substantially simultaneously for every time slot. Typically, the spatial positioning of one or more frames displayed substantially simultaneously may be in a variable order, e.g. an order other than the chronological order that the frames were captured. In one embodiment, each time slot may display all image frames captured from a specified region. For example, the first time slot may include all frames captured in the esophagus, the second time slot may display all images captured in the stomach, etc. In an alternate embodiment the same number of image frames may be displayed in each time frame.

Figure 2:
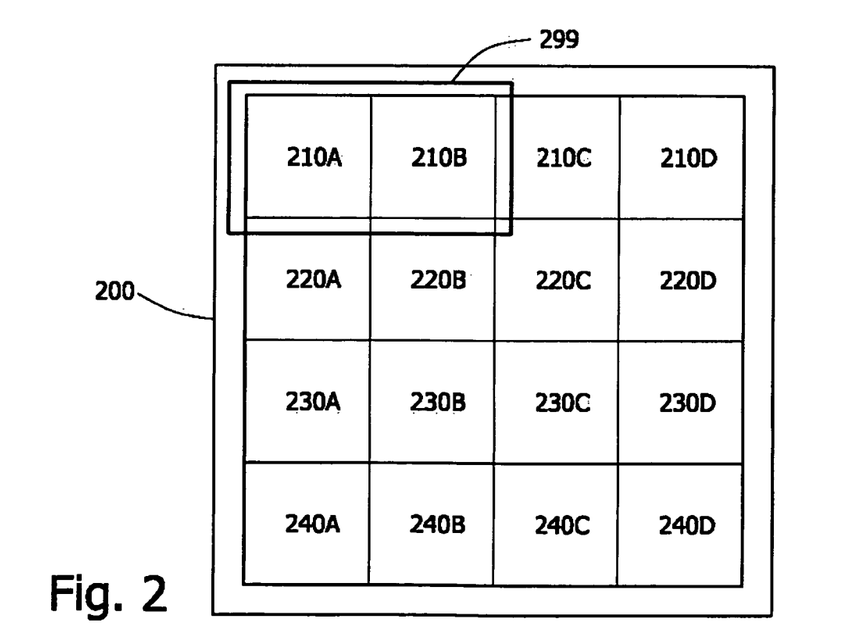
FIG. 2 shows a portion of a display according to an embodiment of the present invention.

FIG. 2 depicts a portion of a display according to an embodiment of the present invention. The display 200 may include, for example, 16 image frames displayed substantially simultaneously in a single time slot (210A-240D). In an exemplary embodiment, the windows or viewing areas, 210A, 210B etc., may be close together, with a minimum of blank or black space between the frames, and typically may be displayed in matrix form, to allow a viewer to see the entirety of the frames without substantially moving his eyes. Other suitable spatial arrangements may be used.

The spatial order or position of the image frames displayed in a single time slot may be adjusted and/or varied based on for example, computations made by processor 19. The spatial order of the image frames displayed substantially simultaneously may correspond to the chronological order in which the images may have been captured, may correspond to an alternate predetermined criteria, to more than one predetermined criteria, or other criteria of interest. In one embodiment of the invention the spatial order or position of the frames displayed may be based on a predetermined criteria, and/or criteria of interest. In one embodiment of the invention, the image frames displayed in a single time slot may be spatially positioned based on a predetermined criterion of, for example color variation. Other criteria, such as focusing, lighting, blood detection, etc. may be used.

Figure 3:
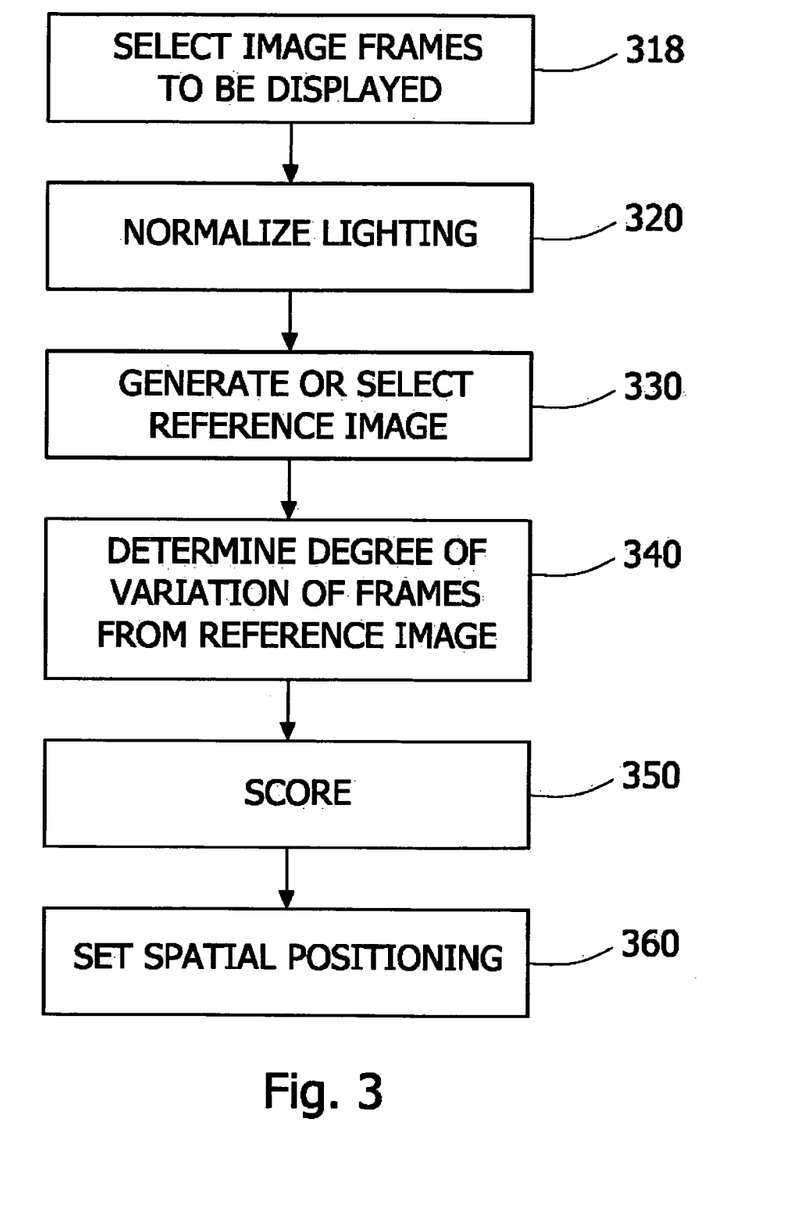
FIG. 3 shows a flow chart describing a method for spatially positioning a plurality of image frames displayed substantially simultaneously, according to an embodiment of the present invention.

An exemplary algorithm is listed in FIG. 3. Referring to block 318, a set of image frames to be displayed substantially simultaneously in a single time slot may be selected. In some embodiments of the present invention, the set of images to be displayed substantially simultaneously in a single time slot may be selected based on for example predetermined criteria. For example, images displaying specified features e.g. color scheme, may be selected to be displayed substantially simultaneously during a single time slot. Other suitable criterion may be used, e.g. focusing, lighting, blood detection, shape features, etc. Normalization or adjustment of lighting may be performed on the image frames to be displayed (block 320). This may be performed to reduce any color variation due to shadowing, variation in lighting intensity, or variation in lighting and image sensor properties when, for example, image frames may be captured from more than one image sensor. Subsequently, a reference image may be generated based on the image frames to be displayed (330). In one embodiment of the invention, the reference image frame may be, for example, an image representing the average or sum of the image frames to be displayed substantially simultaneously in a single time slot. In another embodiment of the present invention, the reference image may be, for example, a selected image frame that may have some known properties, an image selected or generated from a previous time slot, or other suitable images. In one embodiment of the invention, the reference image may represent a typically healthy looking tissue. In step 340, the image frames being displayed in the time slot, may be compared to the generated image. The comparison may be based on comparing sections of images or may be based on comparing whole images. In one example, images displaying pathology may show a high degree of variation with respect to the reference image, for example when the reference image may represent a typically healthy tissue. A score may be given to each image based on the comparison performed (block 350). In another embodiment of the invention, image frames to be displayed in a single time slot may be compared to more than one reference image and receive more than one score. The spatial position of the image frames displayed and/or other suitable parameters, e.g. size may be based on the scores they were assigned (360). For example, according to one embodiment pictures having similar scores may be positioned where a viewer may typically draw his/her eyes first, e.g., at a corner of the display.

Other post processing methods may be included as well to differentiate between images that may display, for example, pathology and images that may display, for example, bubbles, content, or other variations through the GI tract, which may not be associated with pathology or other criteria of interest. In another embodiment of the present invention, the generated image may represent an average image generated from the entire original image stream, from a predetermined section of the original image stream, or from image streams taken from a pool of volunteers. In another example the generated and/or pre-selected image may represent a pathology or specific information that is being sought in the plurality of image streams. As such, images with the lowest degree of variation with respect to the reference image may be representative of the images of interest. Other algorithms may be used as well. As an example, images detected as displaying blood may be a criterion of interest. Algorithms for blood detection have been previously described in U.S. application Ser. No. 10/097,096 filed on Mar. 14, 2002, assigned to the common assignee of the present invention and hereby incorporated by reference. In another embodiment of the invention other criteria besides or together with color variation may be used. For example, shape variation may be used as a criterion to help identify polyps in the GI tract. Variation above or below a certain threshold based on a selected or generated image may be used. The threshold may be adjusted to increase or decrease sensitivity. Other suitable criteria may be used as well.

In yet another embodiment of the invention, the criteria of interest that may determine the spatial order of the image frames in each time slot, and the number of images displayed per time slot may be based on readings concurrently or substantially concurrently obtained from sensors other than image sensor, for example the spatial positioning of image frames displayed substantially simultaneously in a single time slot may be based on reading obtained from one or more non-image sensors mentioned herein.

Figure 4:
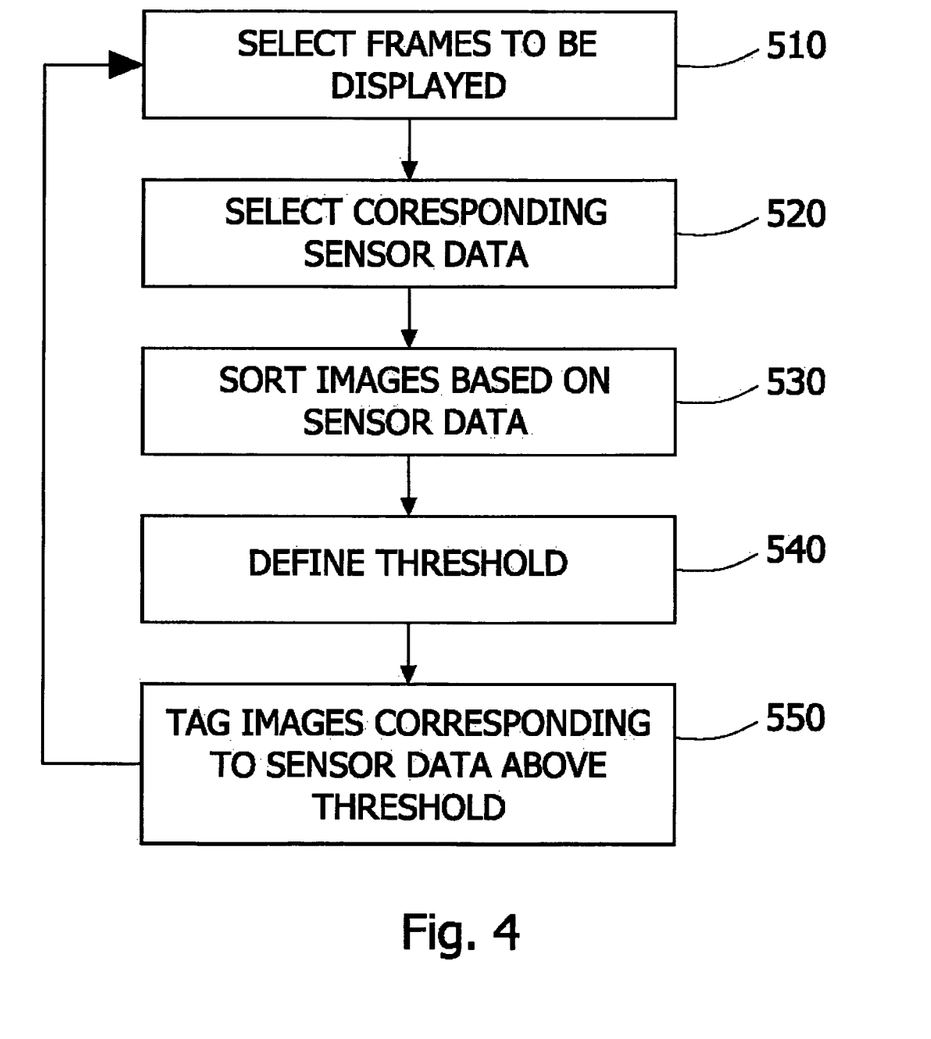
FIG. 4 shows a flow chart describing a method for spatially positioning a plurality of image frames displayed substantially simultaneously, according to another embodiment of the present invention.

In some embodiments of the present invention, in-vivo sensors readings may be used as input, for example, to processor 19, to sort spatial positioning of frames in each time slot. Other suitable methods of determining spatial positioning may be used. Reference is now made to FIG. 4 showing a flow chart for sorting image frames displayed substantially simultaneously in a single time slot. In step 510, images to be displayed substantially simultaneously may be selected. Corresponding sensor readings from one or more non-image sensors (e.g. temperature sensor, pressure sensor, blood sensor, pH sensor, ultrasound sensor, oxygen sensor, etc.) may be selected (step 520). For example, temperature readings recorded during the time of capturing the image frames selected in step 510 may be used. Images selected in step 510 may be sorted (step 530) based on the corresponding sensor data selected in step 520, in for example ascending or descending order. Other methods of sorting may be implemented. In one embodiment of the present invention, sorting may be based on reading of more than one sensor and may be based on image analysis, or image analysis as well as sensor readings. In another embodiment of the present invention, images may also be sorted based on for example a one or zero output of a sensor, so that all images corresponding to a one output may be grouped together and all images corresponding to a zero output may be grouped together. Images corresponding to sensor readings passing a defined threshold may be tagged (540). Such images may be emphasized during display as may be described herein.

Typically, increasing the number of image frames displayed substantially simultaneously in a single time slot, may allow for a processing method such as the examples described in FIG. 3 and FIG. 4 to single out, for example, a relatively small number of frames showing pathology from, for example, a relatively large number of frames showing typically healthy looking tissue. Increasing the number of images displayed in a single time slot may decrease the emphasis on small variation in, for example, healthy tissue while possibly increasing the emphasis on large variations that may appear in for example, pathological tissues. In addition, increasing the number of images displayed in a single time slot may decrease the viewing time and/or the length of the displayed image stream.

In one embodiment of the invention, image frames that may have showed, for example, a high degree of variation may be positioned, for example, on monitor 18, in a location where the user may mostly likely glance first, and image frames that may have shown, for example, a low degree of variation may be positioned, for example, where the user may most likely to glance last. In one embodiment of the present invention, it may be assumed that the user may scan the matrix of images starting at the upper left hand corner. In this embodiment, image frames that may be of interest, for example showing a high degree of variation with respect to frames, for example, representing healthy looking tissue, may be positioned in the upper left hand corner, starting with for example frame 210A (FIG. 2). Image frames that may be of least interest, for example, images showing a low degree of variation with respect to images representing healthy looking tissue, may be positioned in the lower right hand corner, ending with for example with frame 240D (FIG. 2). Frames may be arranged by descending order of degree of variation. The progression from frame 210A to frame 240D may be by row (e.g. 210A, 210B, . . . , 220A, 220B, . . . 230A, . . . 240D), by column (e.g. 210A, 220A, . . . , 210B, 220B, . . . 210C, . . . 240D), or radially (e.g. 210A, 210B, 220B, 220A, 210C, 220C, 230C, 230B, . . . 240D). Other suitable progression series may be used. In another embodiment of the present invention, image frames that may be of interest, for example showing a high degree of variation, may be positioned in the center of the image window, at a height, for example, ⅔ above the bottom, while images showing a low degree of variation may be positioned in the periphery of the image window. The progression from image frames showing a high degree of variation to image frames showing a low degree of variation may be a spiral shaped. Spiral progressions may be clockwise spiral progressions, or counter-clockwise progressions. Other suitable criteria may be used besides degree of variation.

Other suitable image frame arrangements may be used as well. For example, image frames in single time slot that meet a particular criteria of interest above a defined threshold may in one embodiment of the present invention, be grouped together for emphasis, by for example, fusion at the borders to form a single entity, or emphasized by, for example, highlighting, inserting a border around grouped image frames, etc. For example, in FIG. 2 image frames 210A and 210B may be emphasized by border 299. Other number of frames or types of grouping may be used.

Figure 5:
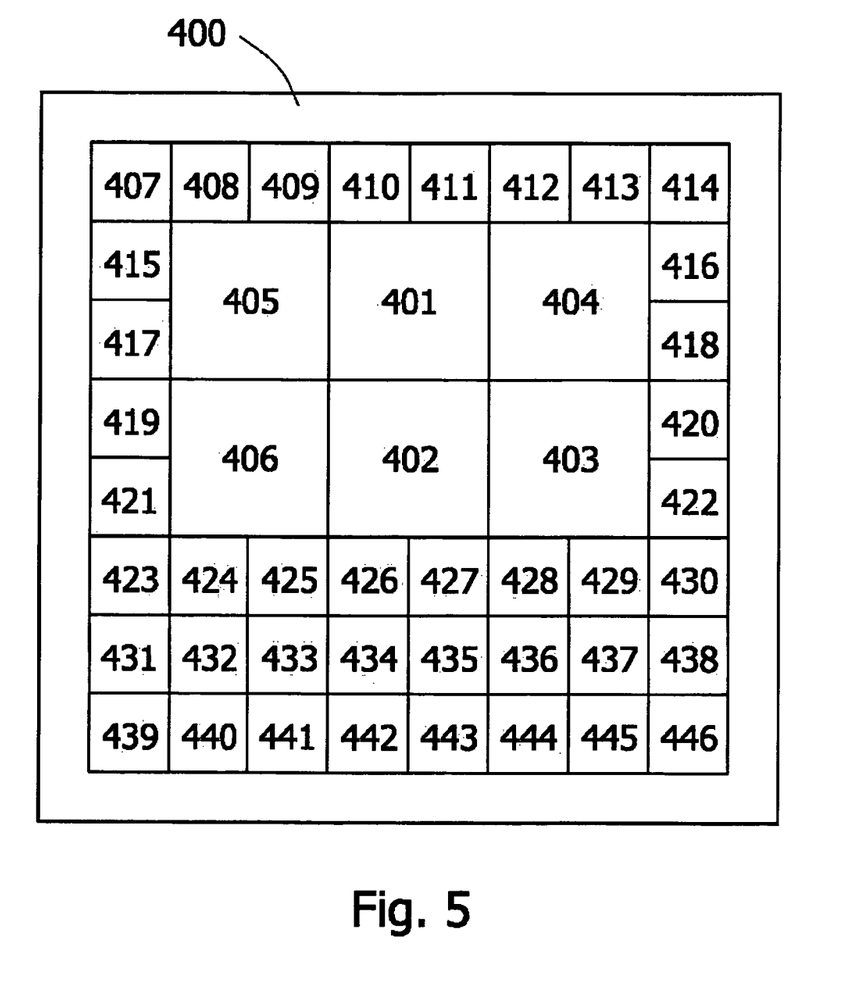
FIG. 5 shows a portion of a display according to a second embodiment of the present invention.

In one embodiment of the invention, images displayed substantially simultaneously may be of different sizes or shapes. In one example, specific images from the group of images displayed substantially simultaneously may be enlarged or displayed in a larger size so as to emphasize them. Reference is now made to FIG. 5 showing as an example, 46 image frames displayed substantially simultaneously. In one embodiment of the invention, image frames having for example, the highest degree of variation according to a specified criteria are placed in, for example the center (with respect to, for example, the horizontal positioning), at a height ⅔ above the bottom. In one example, images with variation above a predetermined threshold may be grouped together and displayed in larger frames such as frames 401, 402, 403, 404, and 405, 406. Other images below the specified threshold, for example, might be displayed in smaller frames such as, for example, frames 407 to 446. The sensitivity of this grouping may be adjusted by increasing or decreasing the defined threshold. The threshold may be adjusted by the user or for example by an algorithm adjusting the threshold based on a defined maximum and minimum number of large frames to be displayed concurrently in a single time slot along with other criteria.

In another embodiment of the invention, the larger frames may be positioned at the top left corner. In yet another embodiment of the present invention different size frames may be positioned in other suitable arrangement. As such, a large number of images may be reviewed by a user, such as a health professional, while only emphasizing the typically few images most likely to contain information of interest. The typically large majority of images less likely to contain information of interest may be reviewed at a quick glance. In one embodiment of the invention, a user may pause the image streaming when identifying an image of particular interest. As such the user may examine more carefully the image or images of interest and the images taken around the vicinity of the image of interest. The order that the images may be shown substantially simultaneously may be altered to show images for example in a chronological order. Other suitable features may be used as well to aid in the analysis of the images obtained.

In one embodiment of the invention, lighter images may be in general positioned in the upper part of the image window 50, (FIG. 1B) while in general darker images may be positioned in the lower end of image window 50. As such the continuity between subsequent time slots may be enhanced for easier viewing of a stream. In other embodiments of the present invention, other suitable parameters may be used for determining the order of the image frame.

Typically, if normally a single-frame stream may be displayed at a certain rate, a multi-frame stream may be displayed at a slower rate. For example if typically a single-frame stream may be displayed at 20 frames per second, a multi-frame stream may be displayed for example at 5 or less frames per second. In such a case the overall viewing time may be up to four times less than the original single-frame stream viewing time. Other suitable viewing rates and ratios between single-frame stream and multi-frame stream viewing time may be used. In one embodiment of the invention, the viewing rate or other viewing parameters of the multi-frame stream may be adjusted based on the content of the frames displayed in each time slot and based on the transition of sequential time slots. For example, time slots including frames that may meet a criterion of interest may be displayed at a slower rate than time slots that may not include frames that meet a criterion of interest. In another example, the viewing rate may be reduced where there may be a large variation in the color content in the transition between neighboring time slots. In yet another embodiment of the invention, a user may adjust the frame rate as well as the number of frames displayed substantially simultaneously.

Figure 7:
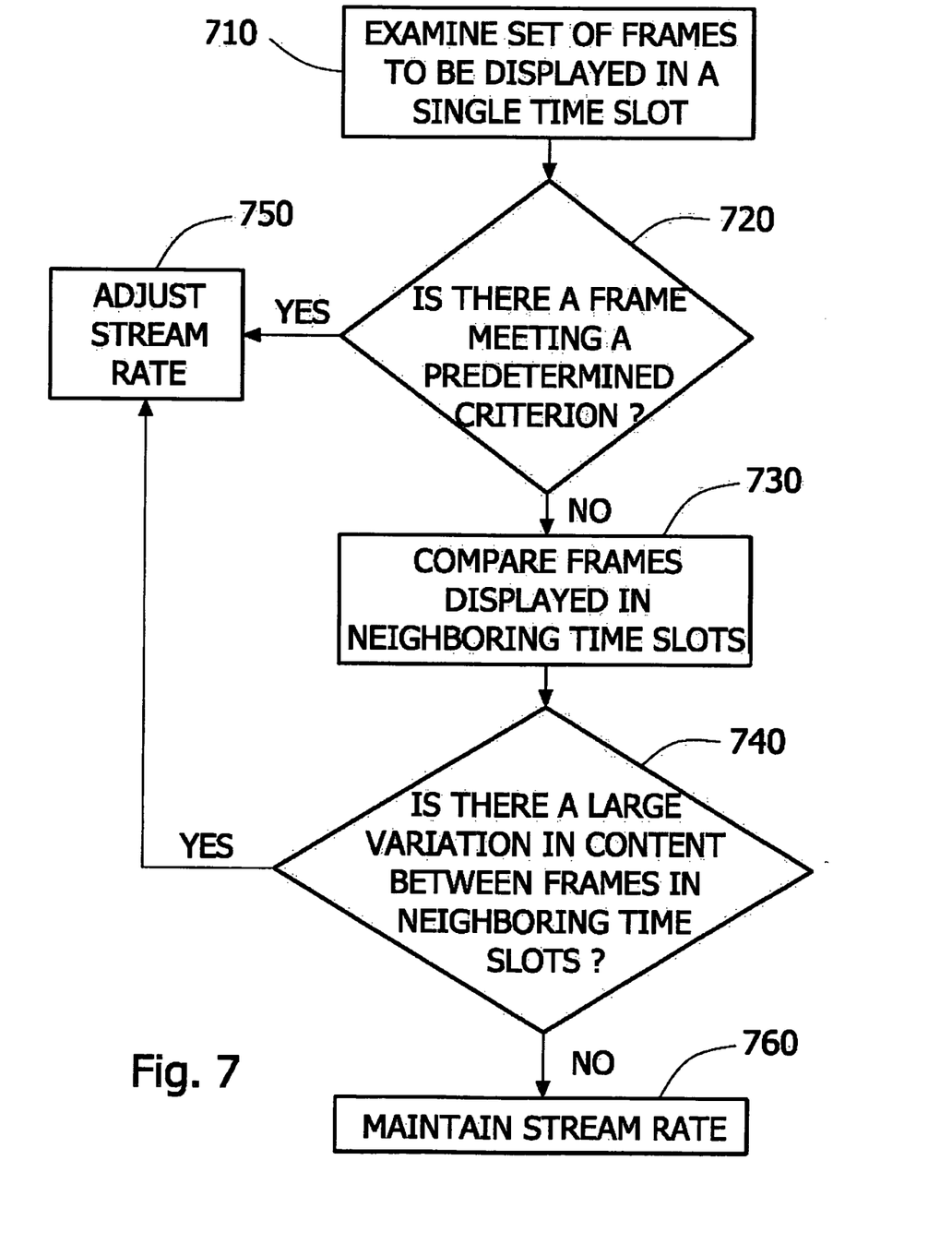
FIG. 7 showing an exemplary flow chart for adjusting the stream rate of the multi-frame stream according to one embodiment of the present invention.

Reference is made to FIG. 7 showing an exemplary flow chart for adjusting the stream rate of the multi-frame stream according to one embodiment of the present invention. In one example, a set of frames to be displayed in a single time slot may be examined (step 710). If one or more frames meet a predetermined criterion (step 720), such as a criterion of interest, the stream rate may be adjusted (step 750), for example, reduced. This may help to further emphasize frames that may be of interest. In another example, the viewing rate may be reduced where there may be a large variation in the color content in the transition between neighboring time slots. Frames displayed in neighboring time slots may be compared (step 730). If there is a large variation in frames displayed in neighboring time slots, for example a large variation in color content or texture, the stream rate may be reduced (step 740). If there is no significant variation and no frames meeting a criterion of interest, the stream rate may be maintained (step 760). In yet another embodiment of the invention, a user may adjust the frame rate as well as the number of frames displayed substantially simultaneously.

In an exemplary embodiment, the user may switch modes, for example between viewing the images as one stream and viewing the images as a plurality of streams using a control such as a keystroke, mouse, or on-screen button. The user may control the plurality of streams in a manner similar to the control of a single stream, for example by using on screen controls. In an alternate embodiment, only one mode may be offered to the user. In yet an alternate embodiment of the invention, a user may select a mode of only viewing images meeting a defined criterion of interest.

In some embodiments, each image may be displayed with different post-processing. For example, one image may be subject to certain filtering or manipulation (e.g., red or green filtering, contrast enhancement, brightness alteration) and the other image may be subject to different or no filtering or manipulation. In one embodiment two or more images in a plurality of streams displayed substantially simultaneously may be fused together, for example, at the borders and may be displayed as a single entity. As such, a user may comfortably and concurrently incorporate information shown in each of the images while avoiding the distraction that may be caused by the typically sharp contrast between connecting edges or between the images and the background color which may appear between the images when the images are spaced apart. According to some embodiments fusing borders between independent images may be accomplished by, for example, one or more post processing algorithms known in the art, including but not limited to, smoothing convolution, mirroring, overlapping, linear or non-linear fade-out fade-in, truncation, linear shape distortion, non-linear shape distortion, normalization or intensity, or other suitable post-processing.

Known image streams captured in a body lumen may typically be displayed and/or reviewed in a chronological order that they may have been captured, e.g. captured at a predetermined and/or set frame rate. According to one embodiment of the present invention, a plurality of image frames captured in a body lumen may be sorted, displayed, streamed and/or view in an order other than the chronological order at which the image frames may have been captured.

Figure 8:
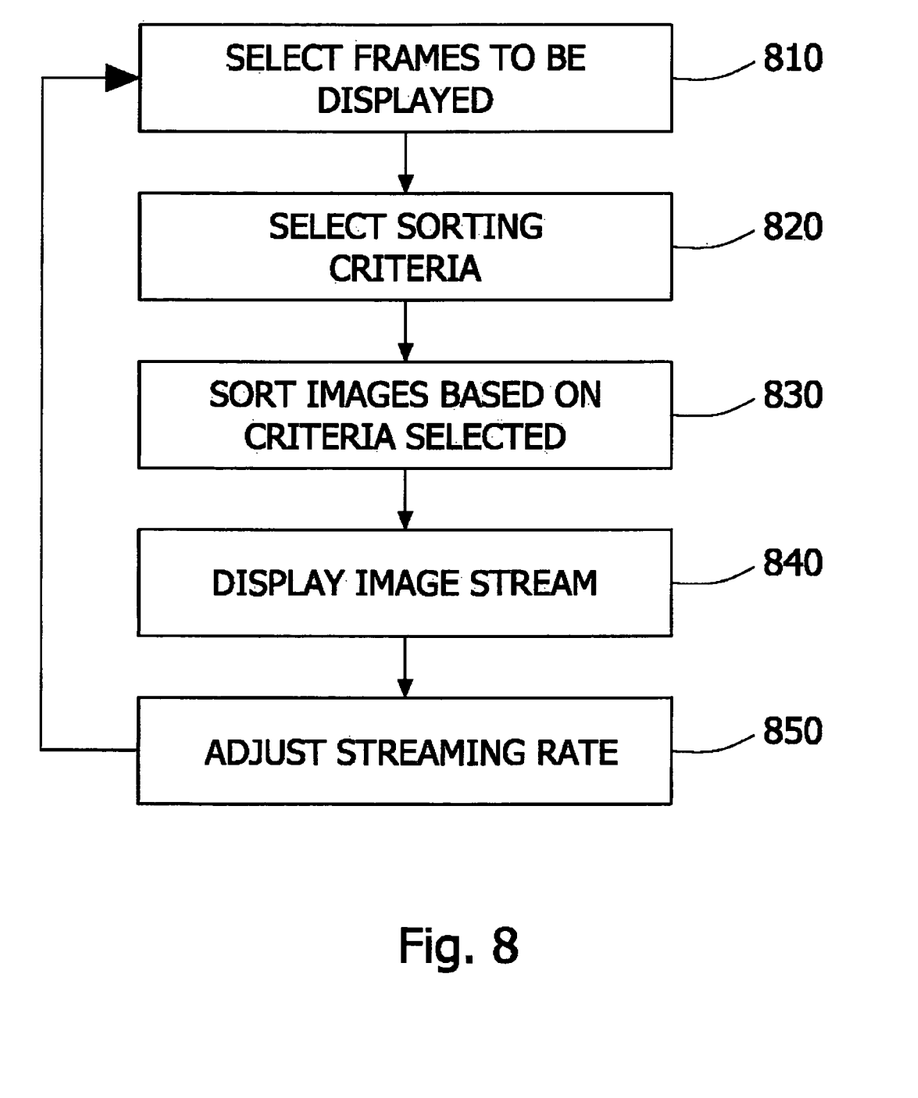
FIG. 8 showing an exemplary flow chart for sorting and displaying a plurality of image frames according to an embodiment of the present invention.

Reference is now made to FIG. 8 showing an exemplary flow chart for sorting and displaying a plurality of image frames according to an embodiment of the present invention. In block 810 image frames to be sorted and displayed may be selected. In some examples, the entire image stream (of the plurality of image frames captured) may be selected. In other examples a segment and/or segments of the image stream (i.e. a subset of the plurality of image frames captured) may be selected.

In block 820, a criterion or criteria for sorting may be selected. According to embodiments of the present invention the criterion for sorting may be any pre-defined suitable criterion, for example, morphological feature, brightness level of an image frame, color, pattern, color scheme, pathological identification, structure identification, etc. In block 830 the plurality of image frames selected may be sorted. Sorting of image frames may be performed by any methods known in the art and/or as may be described herein. In one example, the image frames in the image stream may be divided into a first group of healthy tissue and a second group of pathological tissue, such that the different groups may be streamed, or otherwise displayed one after the other. In another example, the image frames of the image stream may be sorted based on color scheme. For example, image frames may be displayed in color order, e.g. predominantly red may be displayed first, predominantly yellow images may be displayed next, predominantly green, images may be displayed after that, etc. The image stream may be displayed in the sorted order, for example, all images that may be predominantly a first color may be streamed first, all images that may be predominantly a second color may be streamed second, etc.

In another embodiment of the present invention, the viewer may be allowed to select and/or define the sorting criterion. For example, a viewer may select to sort images based on color, brightness level, presence of a particular structural feature, etc. The sorting may be based on the level of variance of the image frame to the sorting criterion. In another example, a user may select images from a database of images and request that the image stream be sorted based on degree of similarity or correspondence with the selected image frames. In yet another example, the image frames may be sorted based on a reading from one or more other sensors, e.g. pH sensors, temperature sensors, etc.

In block 840 the sorted plurality of image frames may be displayed as one or more image streams. In one embodiment of the present invention, sorting an image stream by one or more common features may allow a viewer to review the stream or at least portions of the stream at a faster pace. Viewing an image stream sorted by features may allow smoother viewing with fewer spikes, for example in the image information. This may help reduce the viewing time required to review the image and/or make a diagnosis. In one embodiment of the present invention, the viewer may choose to view a particular section of the image stream that may be of interest. For example, in an example where an image stream may have been sorted based on color, a viewer may choose to view only a section of the image stream with a particular range of colors that may be of interest e.g. that may be of interest for a diagnostic purpose. The sorted image stream may be displayed as a single image stream, as a multiple image stream streamed substantially simultaneously, or groups of images may be displayed substantially together as a static display.

In block 850, the viewing rate of the image stream may be adjusted by the viewer or may be automatically adjusted based on the variance between neighboring image frames in the image stream. For example, for a section of the image stream where the image frames may be very similar to one another and/or may have a high correspondence, the streaming rate of the image frames may be set at a maximum rate or at a relatively high rate. For sections of the image stream where the image frames may not be similar to one another or may have a high variance, the streaming rate may be decreased.

In another example, the streaming rate of the image stream to be displayed may be adjusted based on the correspondence of the image frames to the selected criterion of interest and/or the sorting criterion. For example, a plurality of image frames may be sorted based on color, e.g. the amount of red present in the image frames. According to one example, the streaming rate for images containing a high degree of red or up to a specified amount or percentage of red may be streamed and/or viewed at a slower streaming rate than other image frames to be displayed, e.g. the image frames with relatively less red that may be displayed toward the end of the image stream. Other methods for adjusting the image stream viewing rate may be implemented. Other suitable methods and steps may be implemented.

It will be appreciated by persons skilled in the art that the present invention is not limited by what has been particularly shown and described hereinabove.

The invention claimed is:

1. A method for displaying an image stream captured in-vivo, said method comprising:
   in a computer system:
   selecting a plurality of image frames from an original image stream, wherein the frames used for selecting are arranged in a chronological order from chronological in-vivo capture;

sorting the plurality of image frames arranged in an original image stream in a chronological order in which the frames were captured in-vivo, the frames being sorted based on the level of variance of the content of the frames from a pre-defined criterion to produce a sorted order, said sorted order being different from the chronological order in which the frames were captured and non-chronological;

selecting subsets of image frames from the frames in the sorted order; and displaying the subsets across a series of time-sequential slots as a multi-frame image stream, wherein in each of the time-sequential slots, image frames of a different subset are displayed simultaneously; and adjusting the viewing rate of a subset of image frames based on the difference in color content or texture of the image frames in said subset of image frames in comparison to the content of image frames of a neighboring subset.

2. The method according to claim 1 comprising sorting a subset of the plurality of image frames.

3. The method according to claim 1 wherein the content is a color content of the plurality of image frames.

4. The method according to claim 1 wherein sorting comprises comparing the content of the frames to the content of a selected image frame.

5. The method according to claim 1 wherein the content is a degree of color variation between the plurality of the image frames.

6. The method according to claim 1 wherein the sorting is based on a user selected criterion.

7. A system for displaying an image stream captured in vivo, the system comprising:
an in vivo imaging device to transmit a plurality of image frames having an initial chronological order;
a processor to select a second plurality of image frames from the plurality of image frames, wherein the frames used for selecting are arranged in a chronological order from chronological in-vivo capture, sort the second plurality of image frames arranged in an original image stream in the initial chronological order thereby changing the order of the frames and producing a sorted order; to select subsets of image frames from the frames in the sorted order; and to control the display of the subsets of image frames as a multi-frame image stream; and
a display controlled by said processor to display the subsets of image frames across a series of time-sequential slots as a multi-frame image stream, wherein in each of the time-sequential slots, image frames of a different subset are displayed simultaneously, wherein the processor is to adjust the viewing rate of a subset based on the difference in color content or texture of the image frames in the subset in comparison to the content of image frames of a neighboring subset;
wherein the frames are sorted based on the level of variance of the content of the frames from a pre-defined criterion to produce the sorted order, said sorted order being different from the initial chronological order and non-chronological.

8. The system according to claim 7 wherein the in vivo imaging device is an autonomous capsule.

9. The system according to claim 7 comprising a user input device wherein the user input device is to select a sorting criterion.

10. The system according to claim 7 wherein the plurality of image frames is captured in the GI tract.

11. The method according to claim 1 wherein sorting is based on a criterion of the content of the frames, the criterion selected from the group consisting of: brightness level, morphological feature, pattern, color scheme, pathological identification and structure identification.

12. The system according to claim 7 wherein the processor is to sort based on a criterion of the content of the frames, the criterion selected from the group consisting of: brightness level, morphological feature, pattern, color scheme, pathological identification and structure identification.

13. The method according to claim 1, wherein image frames from the original image stream showing a high degree of similarity are sorted into one section of the sorted order and image frames from the original image stream showing a high degree of variation are sorted into another section of the sorted order.

14. The method according to claim 1 wherein the image frames are sorted into a first group associated with healthy tissue and a second group associated with pathological tissue and image frames associated with pathological tissue are positioned away from image frames associated with healthy tissue in the sorted order.

15. The method according to claim 1 wherein the image frames are sorted based on a reading from one or more non-image sensors.

16. The system according to claim 7 wherein the processor is to sort image frames from the original image stream showing a high degree of similarity into one section of the sorted order and image frames from the original image stream showing a high degree of variation into another section of the sorted order.

17. The system according to claim 7 wherein the processor is to divide image frames into a first group associated with healthy tissue and a second group associated with pathological tissue in the sorted order and image frames associated with pathological tissue are positioned away from image frames associated with healthy tissue.

18. The method according to claim 1, wherein the image frames of each subset displayed substantially simultaneously are positioned in order of degree of variation of the content of each frame from a pre-defined criterion.

19. The system according to claim 7, wherein the image frames of each subset displayed substantially simultaneously are positioned in order of degree of variation of the content of each frame from a pre-defined criterion.

20. A method for displaying an image stream captured in-vivo, said method comprising:
in a computer system:
sorting a plurality of image frames arranged in an original image stream in a chronological order in which the frames were captured in-vivo, the frames being sorted based on the level of variance of the content of the frames from a pre-defined criterion to produce a sorted order, said sorted order being different from the chronological order in which the frames were captured and non-chronological; and
streaming the plurality of image frames across a series of time-sequential slots as a second image stream arranged in the sorted order, wherein in each of the time-sequential slots, image frames of a different subset of said plurality are displayed simultaneously.

21. The method according to claim 20, comprising selecting a subset of the plurality of image frames.

22. The method according to claim 20, wherein the content is a color content of the plurality of image frames.

* * * * *